(12) United States Patent
Rogers

(10) Patent No.: US 8,588,362 B1
(45) Date of Patent: Nov. 19, 2013

(54) APPARATUS AND METHOD FOR DYNAMIC SPECTRAL FILTRATION

(75) Inventor: Carey Shawn Rogers, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 54 days.

(21) Appl. No.: 13/456,742

(22) Filed: Apr. 26, 2012

(51) Int. Cl.
*G01N 23/00* (2006.01)
(52) U.S. Cl.
USPC .................. 378/5; 378/114; 378/156
(58) Field of Classification Search
USPC ............. 378/4, 5, 16, 91, 114, 115, 156, 157, 378/158
See application file for complete search history.

(56) References Cited

U.S. PATENT DOCUMENTS 5,966,426 A * 10/1999 Marra et al. ................. 378/159

OTHER PUBLICATIONS

Primak et al., "Improved dual-energy material discrimination for dual-source CT by means of additional spectral filtration," Medical Physics, vol. 36, No. 4, Apr. 2009, pp. 1359-1369.

* cited by examiner

*Primary Examiner* — Jurie Yun
(74) *Attorney, Agent, or Firm* — Ziolkowski Patent Solutions Group, SC

(57) ABSTRACT

A CT imaging system includes a multi-position x-ray filter having a filter element configured to spectrally filter a beam of x-rays and a magnet structure configured to selectively generate a magnetic field to cause the filter element to move between filter and non-filter positions. A CT imaging system computer causes an x-ray source to emit x-rays at each of a first kVp and a second kVp and control the multi-position x-ray filter to position the filter element in the non-filter position during emission of the x-rays at the first kVp and in the filter position during emission of the x-rays at the second kVp. The computer causes current to be provided to the magnet structure so as to generate a magnetic field configured to move the filter element to the filter and non-filter positions at high frequency, into and out of a path of the beam of x-rays.

21 Claims, 4 Drawing Sheets

APPARATUS AND METHOD FOR DYNAMIC SPECTRAL FILTRATION

BACKGROUND

The present invention relates generally to diagnostic imaging and, more particularly, to a system and method for dynamic spectral filtration for providing an increased separation of mean energies between low and high kVp image acquisitions.

Medical imaging devices comprise x-ray systems, magnetic resonance (MR) systems, ultrasound systems, computed tomography (CT) systems, positron emission tomography (PET) systems, ultrasound, nuclear medicine, and other types of imaging systems. Typically, in CT imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry opening within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction. Such typical systems, however, do not include an ability to discriminate spectral energy content of x-rays as they pass through an object being imaged.

However, as known in the art, dual or multi-energy spectral CT systems have been developed that can reveal the densities of different materials in an object and generate images acquired at multiple monochromatic x-ray energy levels. In the absence of object scatter, a system derives the behavior at a different energy based on a signal from two regions of photon energy in the spectrum: the low-energy and the high-energy portions of the incident x-ray spectrum. In a given energy region of medical CT, two physical processes dominate the x-ray attenuation: (1) Compton scatter and the (2) photoelectric effect. The detected signals from two energy regions provide sufficient information to resolve the energy dependence of the material being imaged and the relative composition of an object composed of two hypothetical materials.

Different approaches have been developed to realize dual energy or spectral imaging. To name a few, dual x-ray source and detector, a single x-ray source with an energy discriminative detector, and a single x-ray source and detector with multiple acquisitions at different kVp or interleaved with fast kVp switching capability are examples of techniques.

In a dual x-ray source and detector system, typically two x-ray sources are provided, each having a respective detector positioned opposite thereto such that x-rays may be emitted from each source having a different spectral energy content. Thus, based on the known energy difference of the sources, a scintillating or energy integrating device may suffice to distinguish energy content and different materials within the object being imaged.

In a single x-ray source with an energy discriminative detector, energy sensitive detectors may be used such that each x-ray photon reaching the detector is recorded with its photon energy. Such systems may use a direct conversion detector material in lieu of a scintillator.

In a single x-ray source and detector arrangement, a conventional third generation CT system may acquire projections sequentially at different peak kilovoltage (kVp) levels, which changes the peak and spectrum of energy of the incident photons comprising the emitted x-ray beams. Two scans are acquired—either (1) back-to-back sequentially in time where the scans require two rotations around the subject (i.e., rotate-rotate), or (2) interleaved as a function of the rotation angle requiring one rotation around the subject, in which the tube operates at, for instance, 80 kVp and 140 kVp potentials.

When dual energy data is acquired in a rotate-rotate fashion, data is collected at a high kV setting over 180 degrees plus ½ the fan angle of the x-ray beam, so as to cover typically about 210 degrees. A short time is then taken to change the kV setting, with around 100 degrees of gantry rotation occurring during this changing (depending on the gantry rotation speed). The second kV dataset is then collected over 180 degrees plus ½ fan angle, so as to again cover typically about 210 degrees. Dual energy data is thus collected in rotate-rotate in less than two full rotations.

When dual energy data is acquired in an interleaved fashion, an input voltage to the x-ray source is switched quickly between the low and high kVp potentials so that a full dataset is collected in 1 rotation, which allows a close correlation between imaging data sets. The high and low kV datasets are thus being continuously collected in a rapid alternating fashion around the patient, with each rotation being divided into approximately 1000 views, so about 350 degrees/1000 views ~0.35 deg/view for each energy level, for example. While acquisition in such an interleaved fashion advantageously provides close temporal registration between the 2 kV datasets so as to minimize artifacts due to patient motion, a drawback to the interleaved acquisition is that, because the switching occurs very rapidly on a single x-ray source, there is little opportunity to change the filtration between the two samples. As a result, there is a spectral (energy) overlap between the two samples that inherently limits the amount of energy separation between them. As known in the art, it is desirable to increase energy separation between low and high kVp operation in order to increase the energy separation of the high and low kV spectrums so as to yield higher dual energy contrast (i.e., increase the contrast between the two materials being evaluated—the "dual energy (DE) ratio"). However, it is not feasible to simply decrease the low kVp or increase the high kVp in order to increase energy separation therebetween. Lowering the low kVp may have limited signal-to-noise and cause other limitations in image reconstruction, with most x-rays get absorbed at lower kV settings (i.e., higher absorbed dose) so as to not make it to the detector. Increasing the high kVp may cause system instability and spit activity and may cause other limitations in system operation, with higher kV also yielding less contrast since fewer x-rays interact with object being imaged.

Therefore, it would be desirable to have a system and method of increasing energy separation in dual energy CT.

BRIEF DESCRIPTION

The present invention is directed to a system and method for providing increased energy separation in dual energy CT.

According to an aspect of the present invention, a CT imaging system includes an x-ray source configured to emit a beam of x-rays toward an object to be imaged, a detector configured to receive the x-rays attenuated by the object, and a multi-position x-ray filter positioned between the x-ray source and the object, with the multi-position x-ray filter further including a filter element configured to spectrally filter the beam of x-rays and a magnet structure configured to selectively generate a magnetic field so as to cause the filter element to move between a filter position and a non-filter position. The CT imaging system also includes a data acquisition system (DAS) operably connected to the detector and a computer operably connected to each of the x-ray source, the x-ray filter, and the DAS, with the computer being programmed to cause the x-ray source to emit x-rays at each of a first kVp and a second kVp toward the detector, control the multi-position x-ray filter to position the filter element in the non-filter position during emission of the x-rays at the first kVp, and control the multi-position x-ray filter to position the filter element in the filter position during emission of the x-rays at the second kVp, wherein positioning the filter element in the filter and non-filter positions comprises causing current to be provided to the magnet structure so as to generate a magnetic field configured to move the filter element to the filter and non-filter positions at high frequency, into and out of a path of the beam of x-rays.

According to another aspect of the present invention, a spectral filter for use in a fast kV switching computed tomography (CT) imaging system that acquires image data at a first kVp setting and a second kVp setting includes a magnet structure configured to selectively generate a magnetic field responsive to a supply of power thereto and a filter element configured to spectrally filter x-rays when an x-ray beam is directed therethrough, wherein the filter element is caused to translate from a non-filter position to a filter position when acted upon by the magnetic field. The spectral filter also includes a controller configured to determine an operational status of an x-ray tube in the CT system, wherein the x-ray tube operates at either the first kVp setting or the second kVp setting in response to a fast kV switching trigger signal being provided thereto. The controller is also configured to control operation of the magnet structure based on the determined operational status of the x-ray tube, wherein controlling operation of the magnet structure comprises causing current to flow to the magnet structure in a first direction when the x-ray tube is operating at the first kVp setting such that the filter element is located in the non-filter position and causing current to flow to the magnet structure in a second direction opposite the first direction when the x-ray tube is operating at the second kVp setting such that such that the filter element is located in the filter position, wherein switching the current flow to the magnet structure between the first and second directions is synchronized with the providing of the fast kV switching trigger signal to the x-ray tube.

According to yet another aspect of the present invention, a method of dual energy CT imaging includes positioning a spectral filter comprising a magnet structure and a filter element between an x-ray source and an object to be imaged and acquiring imaging data with the x-ray source energized to a first kVp potential and with the source energized to a second kVp potential so as to provide for dual energy imaging, with the x-ray source being caused to switch between operation at the first kVp potential and the second kVp potential responsive to a switching trigger signal. The method also includes selectively positioning the filter element in one of a non-filter position and a filter position during acquisition of the imaging data at the first and second kVp potential, wherein selectively positioning the filter element further includes providing current to the magnet structure in a first direction synchronously with providing of a switching trigger signal causing the x-ray source to operate at the second kVp potential such that the magnet source generates a magnetic field configured to position the filter element at the filter position and into a path of a beam of x-rays generated by the x-ray source and providing current to the magnet structure in a second direction synchronously with providing of a switching trigger signal causing the x-ray source to operate at the first kVp potential, such that the filter element is positioned at the non-filter position and out of the path of the beam of x-rays generated by the x-ray source.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION

The operating environment of the present invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
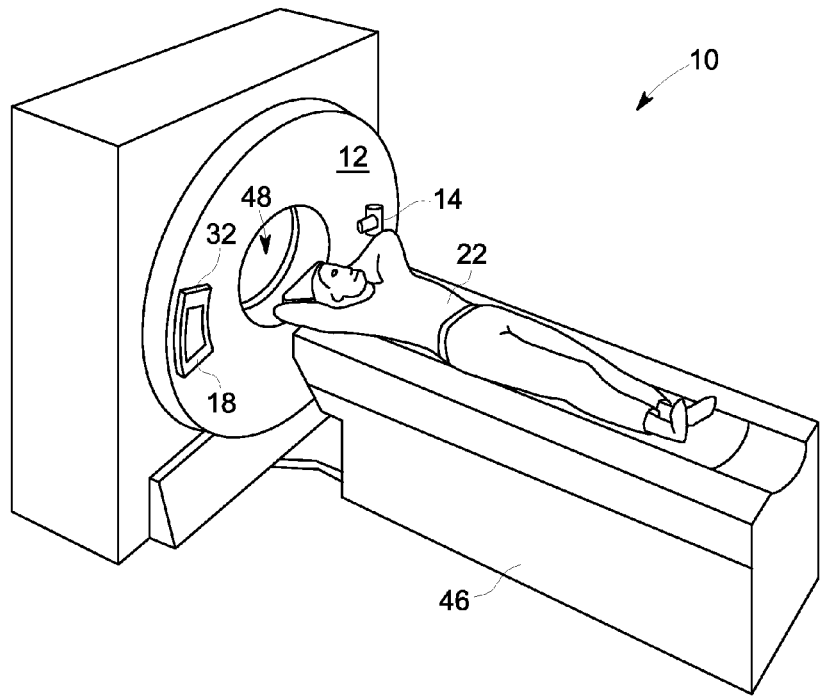
FIG. 1 is a pictorial view of a CT imaging system.
Figure 2:
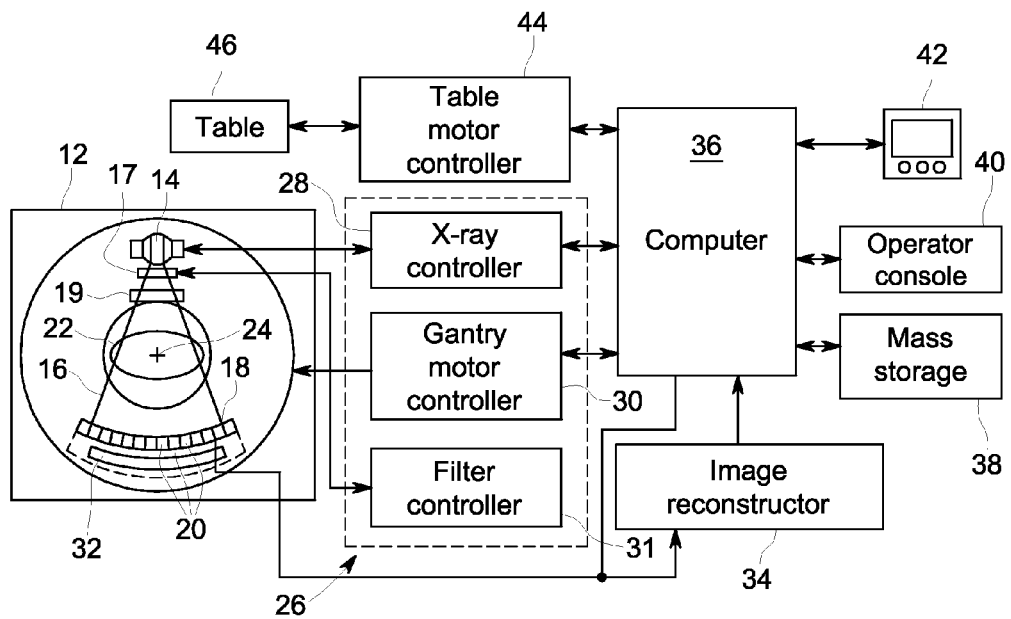
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 through a dynamically controlled multi-position spectral filter 17 and toward a detector assembly or collimator 18 on the opposite side of the gantry 12. The beam of x-rays 16 generated by x-ray source 14 is collimated to desired dimensions by a pre-patient collimator 19, such as by using tungsten blades in front of the x-ray source and different detector apertures, so as to define the size and shape of the beam of x-rays 16 that emerges from the x-ray source 14.

As shown in FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing, with the processed data commonly referred to as projection data or projections. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12, the operation of x-ray source 14, and the operation of multi-position spectral filter 17 are governed by a control mechanism 26 of CT system 10. Control mechanism 26 includes an x-ray controller 28 that provides power and timing signals to an x-ray source 14, a gantry motor controller 30 that controls the rotational speed and position of gantry 12, and a filter controller 31 that controls a positioning of a filter element in the spectral filter 17. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

According to embodiments of the invention, CT system 10 is employed for dual or multi-energy imaging. In dual or multi-energy imaging, two or more sets of projection data are typically obtained for an imaged subject/object at different tube peak kilovoltage (kVp) levels, which change the peak and spectrum of energy of the incident photons comprising the emitted x-ray beams. That is, x-ray source 14 is operated at two or more different tube kVp levels. In one example, low and high kVp spectra are respectively 80 kV and 140 kV, and in one example, the low kVp potential and the high kVp potential are each for a period less than one millisecond. However, it is to be understood that any low and high kVp spectra may be selected for dual or multi-energy imaging, according to the invention. It is also to be understood that one millisecond duration at low and high kVp potentials is an example, and that any length period may be implemented, depending on imaging application, according to the invention.

In dual or multi-energy imaging, the acquired sets of projection data may be used for basis material decomposition (BMD). During BMD, the measured projections are converted to a set of density line-integral projections. The density line-integral projections may be reconstructed to form a density map or image of each respective basis material, such as bone, soft tissue, and/or contrast agent maps (such as water and iodine). The density maps or images may be, in turn, associated to form a volume rendering of the basis material, for example, bone, soft tissue, and/or contrast agent, in the imaged volume.

Thus, dual-energy CT with fast kVp switching is an attractive way of achieving near simultaneous and near co-registered projection samples of two energies. However, because of the fast switching, there is little opportunity to change filtration between samples or otherwise increase energy separation between the low and high kVp energies. Thus, according to an embodiment of the invention, a single dynamically controlled filter that can be selectively applied during the high kVp energy exposure may be employed to increase energy separation between the low and high kVp energies.

Figure 3:
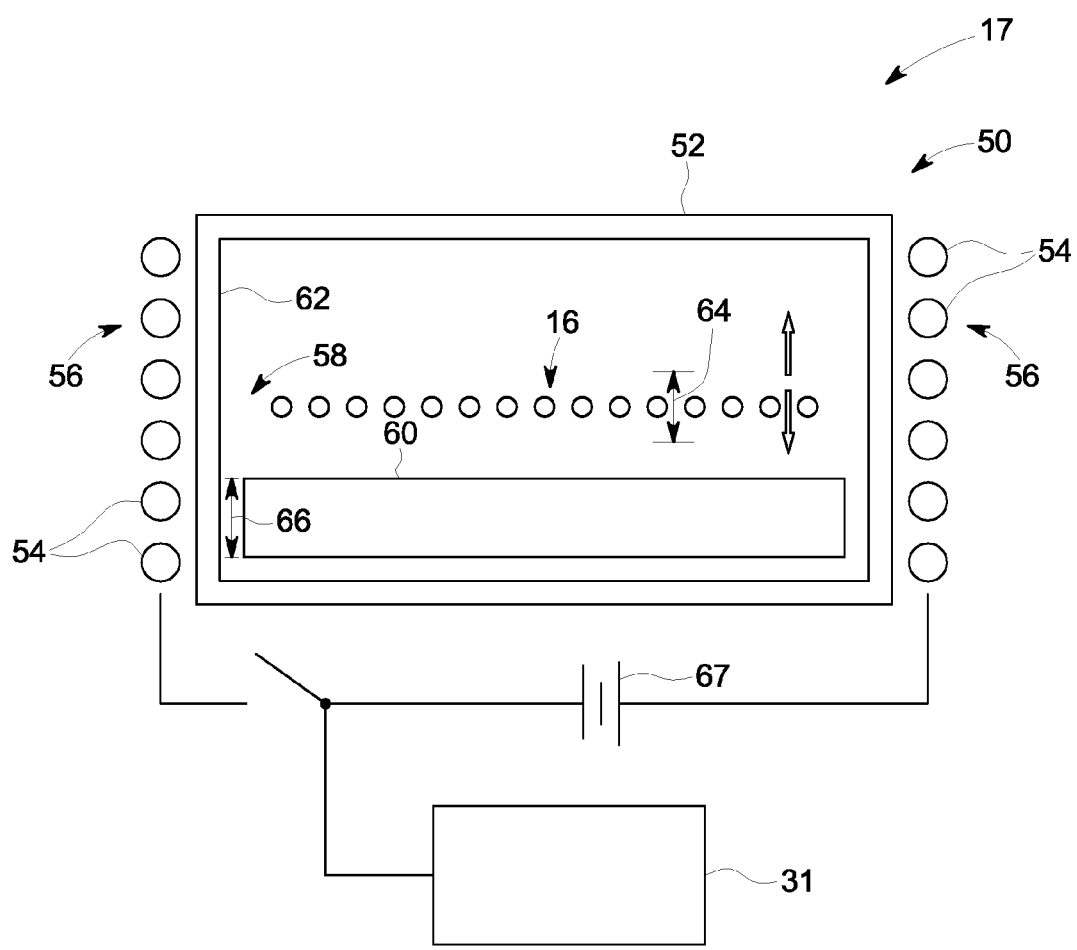
FIG. 3 is an illustration of a multi-position spectral filter for use in the system of FIGS. 1 and 2 according to an embodiment of the invention.

Referring to FIG. 3, a construction of the multi-position spectral filter 17 in CT system 10 of FIGS. 1 and 2 is illustrated in more detail according to one embodiment of the invention. Multi-position spectral filter 17 includes a magnet structure 50 that is controlled to selectively generate a magnetic field. The magnet structure 50 includes a frame 52 constructed of a ferromagnetic material and an electrically conductive coil 54 wrapped around the frame 52. According to one embodiment, the coil 54 is wound about frame 52 to form a solenoid 56 having a helical shape. Together, the frame 52 and solenoid 56 form an electromagnet structure 50 configured to generate a magnetic field when an electric current is passed through the solenoid 56. That is, by providing current to solenoid 56, the magnet structure 50 can be caused to produce a synchronous, bi-directional magnetic field.

The multi-position spectral filter 17 also includes a filter element 58 that is positioned inside of frame 52 and is movable within the frame 52 based on a powered state of the solenoid 56. More specifically, filter element 58 includes a filter foil 60 positioned within a linear bearing housing 62, with the filter foil 60 moving in a sliding motion within linear bearing housing 62 in response to a magnetic field generated by solenoid 56 when an electric current is passed through the solenoid 56. The filter foil 60 is constructed as a solid filter foil of desired thickness (e.g., 1 mm) and may be formed of any of a number of suitable x-ray filtering materials that provide spectral filtration on x-rays passing therethrough. According to embodiments of the invention, filter foil 60 may be formed of tin, molybdenum, copper, for example, or another suitable material. Also, according to the embodiment of multi-position spectral filter 17 shown in FIG. 3, filter foil 60 is constructed to have a uniform thickness as oriented with respect to x-ray beam 16 that passes therethrough.

By selective generation of a magnetic field via powering of the solenoid 56, the position of filter foil 60 can be varied within frame 52 and can be moved into and out of a path of the x-ray beam 16, generally referred to herein and shown in FIG. 3 as a filter position 64 and a non-filter position 66, respectively. For controlling movement and positioning of filter foil at the filter and non-filter positions 64, 66, a controller or computer 31 is provided, such as filter controller 31 in control mechanism 26 in FIG. 2, that selectively controls a supply of power to solenoid 56, thereby also controlling generation of the magnetic field by the magnet structure. The controller 31 selectively controls a supply of current from a power supply 67 to solenoid 56 in a bi-directional manner (i.e., rapidly switches a direction of a current provided to solenoid 56), so as to provide rapid magnetic field switching and so as to enable microsecond placement of filter foil 60 into and out of the path of x-ray beam 16. According to an exemplary embodiment, the magnetic field switching is controlled by controller 31 as described in U.S. patent application Ser. No. 13/096,841, which is herein incorporated by reference, such that eddy current development is controlled to enable the fast switching. Accordingly, the filter foil 60 can be inserted into the x-ray beam 16 (i.e., at the filter position) during the high kVp exposure and can be removed from the x-ray beam 16 (i.e., at the non-filter position) during the low kVp exposure, with the insertion/removal of the filter foil 60 occurring at a high frequency, such as a rate of 1-5 kHz, for example.

According to an exemplary embodiment of the invention, controller 31 synchronizes the switching/reversing of the current direction through solenoid 56, and the corresponding alternating of the force direction of the magnetic field that moves filter foil 60, with the providing of a fast kV trigger signal that switches operation of the x-ray source 14 (FIGS. 1 and 2) between the low and high kV potentials, such that a direction of the bi-directional magnetic field is switched at a selected frequency matching a data acquisition frequency of the CT imaging system. Specifically, when a kV trigger signal is provided to switch the x-ray source 14 from the low kV potential to the high kV potential, controller 31 causes current flowing in a first direction to be provided to solenoid 56 such that magnet structure 50 is energized to generate a magnetic field and corresponding force direction that causes filter foil 60 to move to the filter position 64, into the path of the x-ray beam 16, such that spectral filtration of the x-ray beam is provided thereby. When a kV trigger signal is provided to switch the x-ray source 14 from the high kV potential to the low kV potential, controller 31 causes current flowing in a second direction (opposite the first direction) to be provided to solenoid 56 such that magnet structure 50 is energized to generate a magnetic field and corresponding force direction that causes filter foil 60 to move to the non-filter position 66, out of the path of the x-ray beam 16. Accordingly, controller 31 enables synchronized deployment of filtration of the x-ray beam 16 during high kV exposure.

Figure 4:
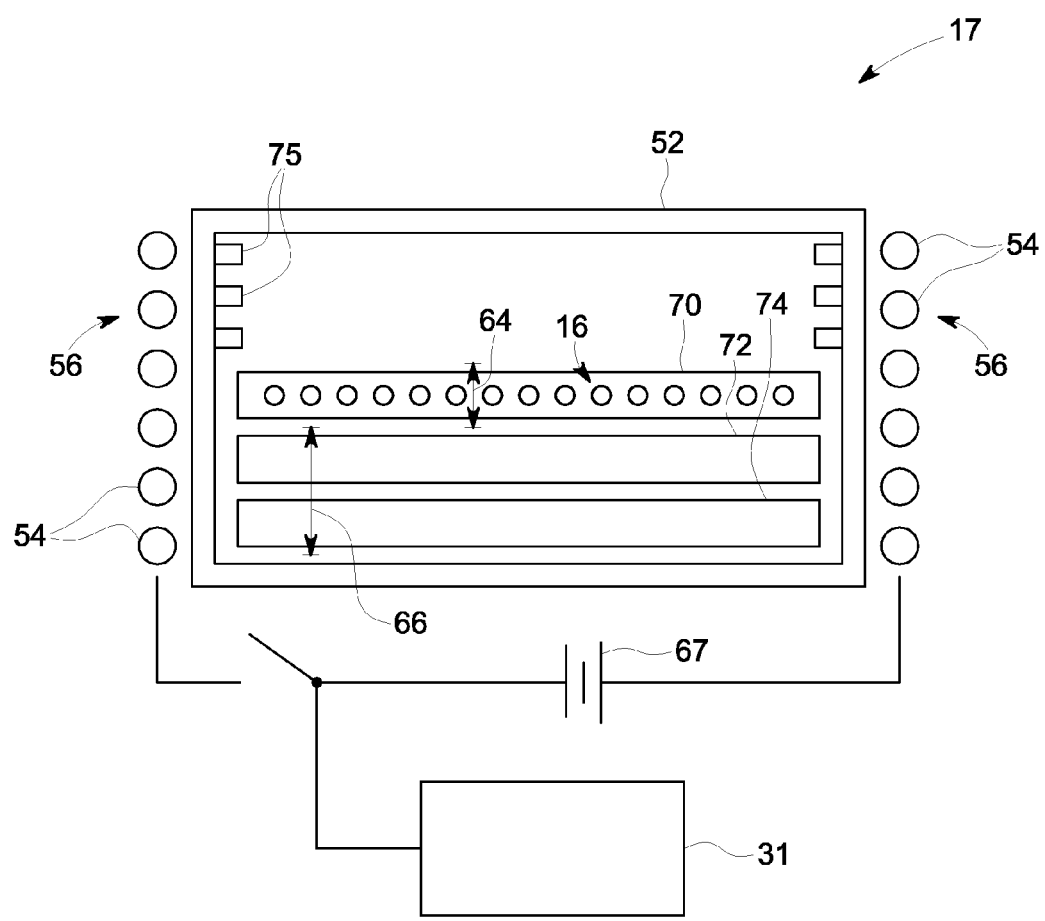
FIG. 4 is an illustration of a multi-position spectral filter for use in the system of FIGS. 1 and 2 according to another embodiment of the invention.

Referring now to FIG. 4, a construction of the multi-position spectral filter 17 in CT system 10 of FIGS. 1 and 2 is illustrated in more detail according to another embodiment of the invention. In the embodiment of FIG. 4, rather than having a single filter foil (such as filter foil 60 in FIG. 3), multi-position spectral filter 17 includes multiple solid filter foils 70, 72, 74 positioned within linear bearing 62. While three filter foils 70, 72, 74 are shown in FIG. 4, it is envisioned that a greater or lesser number of filter foils could be included in spectral filter 17. Each of filter foils 70, 72, 74 is formed of a different material, such that each of the filter foils provides a different level/range of spectral filtration. For example, filter foils 70, 72, 74 could be formed of tin, molybdenum, and copper, respectively, although it is recognized that the filter foils could be made of other suitable materials.

A shown in FIG. 4, according to one embodiment, mechanical stops 75 are provided within frame 52 along with a controller 31 in order to position filter foils 70, 72, 74 within frame 52 at desired locations. By selective generation of a magnetic field via the selective control of a bi-directional flow of current through the solenoid 56, the position of the filter foils 70, 72, 74 can be varied within frame 52, such that each of the filter foils 70, 72, 74 is in a filter position 64 or a non-filter position 66, respectively. According to an exemplary embodiment, controller 31 and mechanical stops 75 function to control positioning of the filter foils 70, 72, 74 in an indexable fashion by selectively controlling the direction of current flow through solenoid 56, thereby also controlling the magnetic force induced on filter foils 70, 72, 74 by the magnet structure. The controller 31 functions to cause a controlled current to be provided to solenoid 56 so as to control the parameters of the magnetic field generated by magnet structure 50, thereby positioning each of filter foils 70, 72, 74 in one of a number of indexed positions. The controller 31 and mechanical stops indexably control positioning of the filter foils 70, 72, 74, such that one of the filter foils is positioned in the filter position, in the path of the beam of x-rays, during emission of the x-rays at the second kV (i.e., high kV), while the other filter foils are in a non-filter position. During emission of the x-rays at the first kV (i.e., low kV), controller 31 indexably controls positioning of the filter foils 70, 72, 74 such that all of the filter foils are in a non-filter position.

In operation, current is provided to solenoid 56 to cause the filter foils 70, 72, 74 to move toward a desired indexed position, with current then being reversed through solenoid 56 in order to apply a braking force to filter foils 70, 72, 74 as they approach a mechanical stop 75. This reversing of current to through solenoid 56 beneficially brakes the filter foils 70, 72, 74 and prevents them from slamming into the mechanical stop 75, thereby preventing damage to the foils and reducing the amount of noise that is generated.

Figure 5:
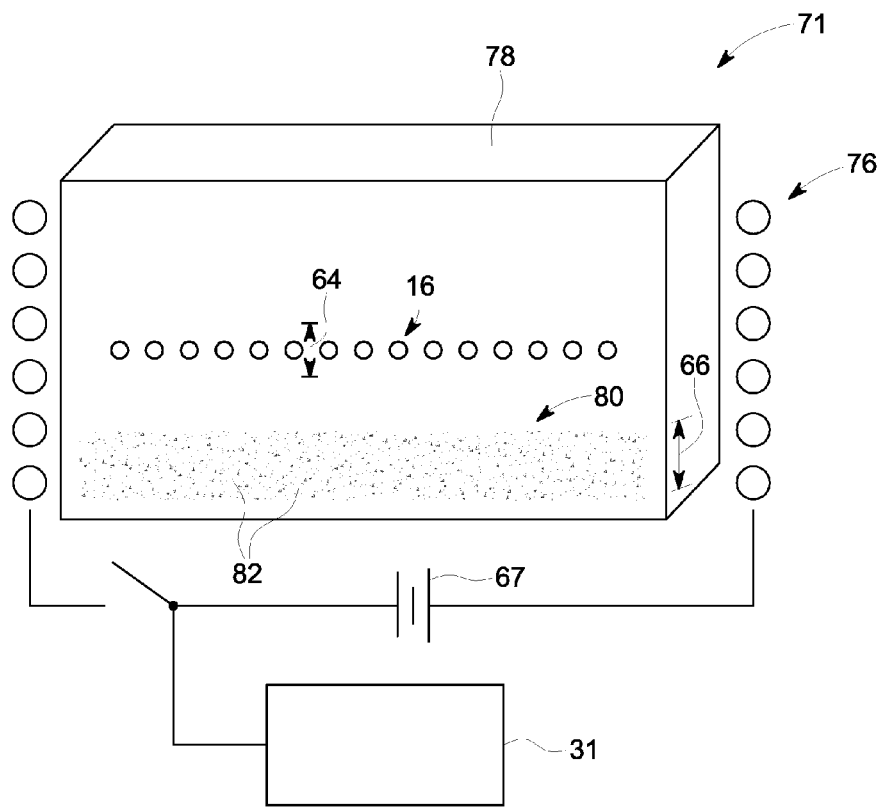
FIG. 5 is an illustration of a multi-position spectral filter for use in the system of FIGS. 1 and 2 according to another embodiment of the invention.

Referring now to FIG. 5, a construction of the multi-position spectral filter 17 in CT system 10 of FIGS. 1 and 2 is illustrated according to still another embodiment of the invention. Multi-position spectral filter 17 includes a magnet structure 76 that is controlled to selectively generate a magnetic field. The magnet structure 76 is in the form of a solenoid or dipole type magnetic structure, according to embodiments of the invention. The magnet structure 76 is formed about an evacuated housing 78 (i.e., housing 78 encloses a vacuum or low pressure gas), with the housing 78 being formed of an x-ray filtering material.

The multi-position spectral filter 17 also includes a filter element 80 that is positioned inside of evacuated housing 78 and is movable within the housing based on a powered state of the magnet structure 76. As shown in FIG. 5, the filter element 80 is in the form of a powderized filter material 82 composed of micro- to nano-scale particles. The powderized filter material 82 has ferromagnetic properties, such that it interacts with the magnetic field generated by magnet structure 76, and may be formed of any of a number of suitable ferromagnetic x-ray filtering materials that provide spectral filtration on x-rays passing therethrough. An anti-agglomeration additive (not shown) is also included in powderized filter material 82 to maintain separation of the particles, so as to enable efficient interaction between the ferromagnetic powderized filter material 82 and the magnetic field.

By selectively controlling a magnetic field via powering of the magnet structure 76 (i.e., controlling direction of a current provided to magnet structure 76), the position of powderized filter material 82 can be varied within evacuated housing 78. The powderized filter material 82 can thus be positioned into and out of a path of the x-ray beam 16 into a filter position 64 and a non-filter position 66 respectively, with an amount of the powderized filter material 82 that is moved into the filter position 64 (i.e., a thickness of the filter element) being determined by the dimensions of the vacuum housing 78. For controlling movement and positioning of powderized filter material 82, a controller 31 controls a supply of current to the magnet structure 76 for selectively controlling parameters of the magnetic field that is generated. The controller 31 selectively controls a direction of current provided from a power supply 67 to magnet structure 76 in a rapid manner so as to enable microsecond placement of powderized filter material 82 into and out of the path of x-ray beam 16. According to an exemplary embodiment, the selective spectral filtration provided by movement of the powderized filter material 82 between the filter and non-filter positions 64, 66 is synchronized with the providing of the fast kV trigger signal that switches operation of the x-ray source 14 (FIGS. 1 and 2) between the low and high kV potentials, with the powderized filter material 82 being caused to move into the filter position 64 via interaction thereof with the magnetic field upon a kV trigger signal being provided that switches the x-ray source 14 from the low kV potential to the high kV potential. Beneficially, as filter element 80 is formed of powderized filter material 82, no reversing of current through solenoid 56 for purposes of generating a braking force is required, as is needed with a solid filter foil.

Figure 6:
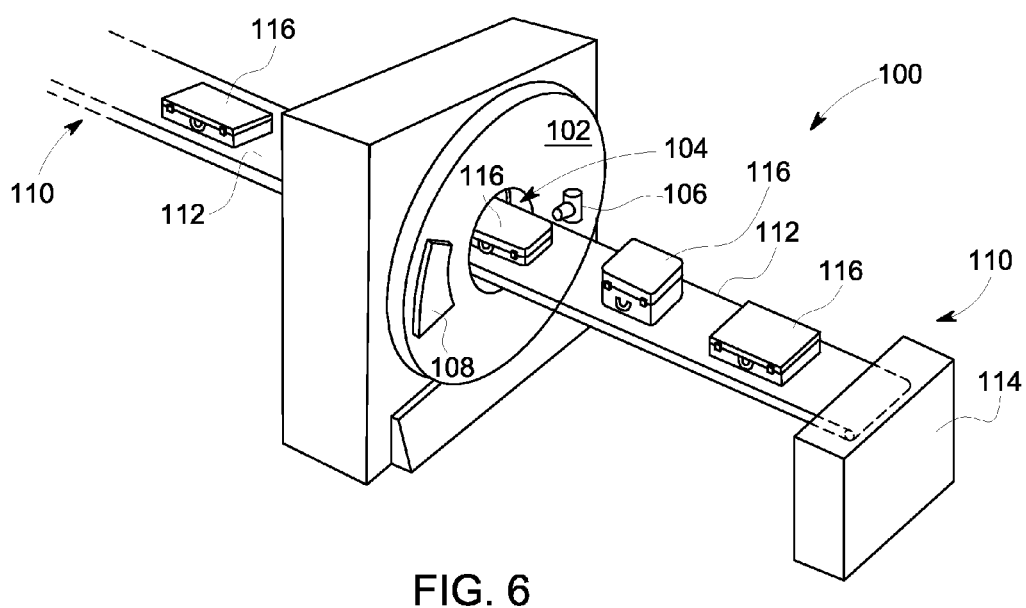
FIG. 6 is a pictorial view of a CT system for use with a non-invasive package inspection system.

Referring now to FIG. 6, package/baggage inspection system 100 includes a rotatable gantry 102 having an opening 104 therein through which packages or pieces of baggage may pass. The rotatable gantry 102 houses an x-ray and/or high frequency electromagnetic energy source 106 as well as a detector assembly 108 having scintillator arrays comprised of scintillator cells. A conveyor system 110 is also provided and includes a conveyor belt 112 supported by structure 114 to automatically and continuously pass packages or baggage pieces 516 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc. An exemplary implementation can aid in the development of automatic inspection techniques, such as explosive detection in luggage.

Beneficially, embodiments of the invention provide increased energy separation between the low and high kVp energies in dual energy CT. The view-view dynamic spectral filtration provided by multi-position spectral filter 17 and the moving of the filter element between the filter and non-filter positions provides for greater spectrum separation between high and low energy (i.e., high kVp and low kVp) data acquisitions, with the filter element being inserted into the x-ray beam during the high kVp exposure and removed during the low kVp exposure. Placement of the filter element in such a filter position and a non-filter position is achieved via rapid magnetic field switching (e.g., less than 20 microseconds) that is provided by a magnet structure positioned about the filter element. The control of the magnet structure is synchronized to the fast kV switching trigger signal, so as to provide synchronized deployment of filtration in the x-ray beam during the high kV exposure. Significant improvement to fast kV switching CT scanning is thus provided, with the spectral filtration capabilities being equivalent to dual energy systems that use two x-ray tubes and detectors with one of the tubes running at high kV with the additional filtration. Embodiments of the current invention thus provide a distinct advantage to spatial and temporal resolution in the fast kV switching mode relative to the two tube-two detector arrangement.

Therefore, according to an embodiment of the invention, a CT imaging system includes an x-ray source configured to emit a beam of x-rays toward an object to be imaged, a detector configured to receive the x-rays attenuated by the object, and a multi-position x-ray filter positioned between the x-ray source and the object, with the multi-position x-ray filter further including a filter element configured to spectrally filter the beam of x-rays and a magnet structure configured to selectively generate a magnetic field so as to cause the filter element to move between a filter position and a non-filter position. The CT imaging system also includes a data acquisition system (DAS) operably connected to the detector and a computer operably connected to each of the x-ray source, the x-ray filter, and the DAS, with the computer being programmed to cause the x-ray source to emit x-rays at each of a first kVp and a second kVp toward the detector, control the multi-position x-ray filter to position the filter element in the non-filter position during emission of the x-rays at the first kVp, and control the multi-position x-ray filter to position the filter element in the filter position during emission of the x-rays at the second kVp, wherein positioning the filter element in the filter and non-filter positions comprises causing current to be provided to the magnet structure so as to generate a magnetic field configured to move the filter element to the filter and non-filter positions at high frequency, into and out of a path of the beam of x-rays.

According to another embodiment of the invention, a spectral filter for use in a fast kV switching computed tomography (CT) imaging system that acquires image data at a first kVp setting and a second kVp setting includes a magnet structure configured to selectively generate a magnetic field responsive to a supply of power thereto and a filter element configured to spectrally filter x-rays when an x-ray beam is directed therethrough, wherein the filter element is caused to translate from a non-filter position to a filter position when acted upon by the magnetic field. The spectral filter also includes a controller configured to determine an operational status of an x-ray tube in the CT system, wherein the x-ray tube operates at either the first kVp setting or the second kVp setting in response to a fast kV switching trigger signal being provided thereto. The controller is also configured to control operation of the magnet structure based on the determined operational status of the x-ray tube, wherein controlling operation of the magnet structure comprises causing current to flow to the magnet structure in a first direction when the x-ray tube is operating at the first kVp setting such that the filter element is located in the non-filter position and causing current to flow to the magnet structure in a second direction opposite the first direction when the x-ray tube is operating at the second kVp setting such that such that the filter element is located in the filter position, wherein switching the current flow to the magnet structure between the first and second directions is synchronized with the providing of the fast kV switching trigger signal to the x-ray tube.

According to yet another embodiment of the invention, a method of dual energy CT imaging includes positioning a spectral filter comprising a magnet structure and a filter element between an x-ray source and an object to be imaged and acquiring imaging data with the x-ray source energized to a first kVp potential and with the source energized to a second kVp potential so as to provide for dual energy imaging, with the x-ray source being caused to switch between operation at the first kVp potential and the second kVp potential responsive to a switching trigger signal. The method also includes selectively positioning the filter element in one of a non-filter position and a filter position during acquisition of the imaging data at the first and second kVp potential, wherein selectively positioning the filter element further includes providing current to the magnet structure in a first direction synchronously with providing of a switching trigger signal causing the x-ray source to operate at the second kVp potential such that the magnet source generates a magnetic field configured to position the filter element at the filter position and into a path of a beam of x-rays generated by the x-ray source and providing current to the magnet structure in a second direction synchronously with providing of a switching trigger signal causing the x-ray source to operate at the first kVp potential, such that the filter element is positioned at the non-filter position and out of the path of the beam of x-rays generated by the x-ray source.

The present invention has been described in terms of the preferred embodiment, and it is recognized that equivalents, alternatives, and modifications, aside from those expressly stated, are possible and within the scope of the appending claims.

What is claimed is:

1. A computed tomography (CT) imaging system comprising:
   an x-ray source configured to emit a beam of x-rays toward an object to be imaged;
   a detector configured to receive the x-rays attenuated by the object;
   a multi-position x-ray filter positioned between the x-ray source and the object, the multi-position x-ray filter comprising:
      a filter element configured to spectrally filter the beam of x-rays; and
      a magnet structure configured to selectively generate a magnetic field so as to cause the filter element to move between a filter position and a non-filter position;
   a data acquisition system (DAS) operably connected to the detector; and
   a computer operably connected to each of the x-ray source, the x-ray filter, and the DAS, the computer being programmed to:
      cause the x-ray source to emit x-rays at each of a first kVp and a second kVp toward the detector;
      control the multi-position x-ray filter to position the filter element in the non-filter position during emission of the x-rays at the first kVp; and
      control the multi-position x-ray filter to position the filter element in the filter position during emission of the x-rays at the second kVp;
      wherein positioning the filter element in the filter and non-filter positions comprises causing current to be provided to the magnet structure so as to generate a magnetic field configured to move the filter element to the filter and non-filter positions at high frequency, into and out of a path of the beam of x-rays.

2. The CT imaging system of claim 1 wherein the magnet structure comprises:
   a ferromagnetic frame configured to house the filter element therein; and
   a solenoid wrapped around the ferromagnetic frame;
   wherein the solenoid and the ferromagnetic frame generate a synchronous, bi-directional magnetic field when the current is supplied to the solenoid in alternating directions and at a selected frequency matching a data acquisition frequency of the CT imaging system.

3. The CT imaging system of claim 2 wherein the filter element comprises at least one solid material filter foil positioned in a linear bearing housing within the ferromagnetic frame, the at least one solid material filter foil being translatable along the linear bearing housing between the filter position and the non-filter position responsive to the magnetic field generated by the solenoid and the ferromagnetic frame.

4. The CT imaging system of claim 3 wherein the computer is programmed to control a direction of the current provided to the solenoid so as to control a direction of a force generated by the magnetic field and move the at least one solid material filter foil to the filter and non-filter positions, into and out of the path of the beam of x-rays.

5. The CT imaging system of claim 3 wherein the at least one filter foil comprises:
   a first solid filter foil composed of a first material; and
   a second solid filter foil composed of a second material that provides different spectral filtration than the first material.

6. The CT imaging system of claim 5 wherein the frame further comprises mechanical stops configured to indexably control positioning of the first solid filter foil and the second solid filter foil, such that one of the first solid filter foil and the second solid filter foil is positioned in the filter position, into the path of the beam of x-rays, during emission of the x-rays at the second kVp.

7. The CT imaging system of claim 6 wherein the computer is programmed to reverse the direction of the current to the solenoid in order to apply a braking force to the first and second filter foils as they approach the mechanical stops.

8. The CT imaging system of claim 1 wherein the magnet structure comprises one of a solenoid structure and a dipole structure formed about a housing that encloses a vacuum or low pressure gas; and
   wherein the filter element comprises a powderized filter material having ferromagnetic properties included inside the housing.

9. The CT imaging system of claim 8 wherein the computer is programmed to cause current to be provided to the one of the solenoid structure and the dipole structure so as to generate a magnetic field configured to move the powderized filter material to the filter and non-filter positions, into and out of the path of the beam of x-rays.

10. The CT imaging system of claim 8 wherein the magnetic powder comprises nano- or micro-sized particles and includes an anti-aggolomeration additive.

11. The CT imaging system of claim 1 wherein the first kVp is approximately 80 kVp and the second kVp is approximately 140 kVp, and wherein the x-rays emitted at the second kVp are emitted immediately subsequent to the x-rays emitted at the first kVp.

12. The CT imaging system of claim 1 wherein movement of the filter element between the filter position and the non-filter position is synchronized with switching of the x-ray source between the first kVp and the second kVp, such that the filter element is in the filter position only during emission of the x-rays at the second kVp.

13. A spectral filter for use in a fast kV switching computed tomography (CT) imaging system that acquires image data at a first kVp setting and a second kVp setting that is higher than the first kVp setting, the spectral filter comprising:
   a magnet structure configured to selectively generate a magnetic field responsive to a supply of power thereto;
   a filter element configured to spectrally filter x-rays when an x-ray beam is directed therethrough, wherein the filter element is caused to translate from a non-filter position to a filter position when acted upon by the magnetic field; and
   a controller configured to:
      determine an operational status of an x-ray tube in the CT system, wherein the x-ray tube operates at either the first kVp setting or the second kVp setting in response to a fast kV switching trigger signal being provided thereto;
      control operation of the magnet structure based on the determined operational status of the x-ray tube, wherein controlling operation of the magnet structure comprises:
         causing current to flow to the magnet structure in a first direction when the x-ray tube is operating at the first kVp setting, such that the filter element is located in the non-filter position; and
         causing current to flow to the magnet structure in a second direction opposite the first direction when the x-ray tube is operating at the second kVp setting, such that such that the filter element is located in the filter position;

wherein switching the current flow to the magnet structure between the first and second directions is synchronized with the providing of the fast kV switching trigger signal to the x-ray tube.

14. The spectral filter of claim 13 wherein the magnet structure comprises:

a ferromagnetic frame configured to house the filter element therein; and a solenoid wrapped around the ferromagnetic frame;

wherein the solenoid and the ferromagnetic frame generate a synchronous, bi-directional magnetic field when a current is supplied to the solenoid in alternating directions and at a selected frequency matching a data acquisition frequency of the CT imaging system.

15. The spectral filter of claim 14 wherein the filter element comprises a solid filter foil positioned in a linear bearing housing within the ferromagnetic frame, the solid filter foil being translatable along the linear bearing housing between the filter position and the non-filter position responsive to the magnetic field generated by the solenoid and the ferromagnetic frame.

16. The spectral filter of claim 14 wherein the filter element comprises a plurality of solid filter foils, the plurality of solid filter foils being composed of a plurality of materials that each provide a different level of spectral filtration.

17. The spectral filter of claim 16 wherein the frame further comprises mechanical stops positioned thereon; and wherein the mechanical stops and the controller are configured to indexably control positioning of the plurality of solid filter foils such that only one of the plurality of solid filter foils is positioned in the filter position at a given time, into the path of the beam of x-rays.

18. The spectral filter of claim 13 wherein the magnet structure comprises one of a solenoid structure and a dipole structure formed about a housing that encloses a vacuum; and wherein the filter element comprises a powderized filter material having ferromagnetic properties that is included inside the housing, the powderized filter material being caused to translate to the filter and non-filter positions.

19. A method of dual energy CT imaging comprising:

positioning a spectral filter between an x-ray source and an object to be imaged, the spectral filter comprising a magnet structure and a filter element;

acquiring imaging data with the x-ray source energized to a first kVp potential and with the source energized to a second kVp potential so as to provide for dual energy imaging, with the x-ray source being caused to switch between operation at the first kVp potential and the second kVp potential responsive to a switching trigger signal; and selectively positioning the filter element in one of a non-filter position and a filter position during acquisition of the imaging data at the first and second kVp potential, wherein selectively positioning the filter element comprises:

providing current to the magnet structure in a first direction synchronously with providing of a switching trigger signal causing the x-ray source to operate at the second kVp potential, such that the magnet structure generates a magnetic field configured to position the filter element at the filter position and into a path of a beam of x-rays generated by the x-ray source; and providing current to the magnet structure in a second direction synchronously with providing of a switching trigger signal causing the x-ray source to operate at the first kVp potential, such that the filter element is positioned at the non-filter position and out of the path of the beam of x-rays generated by the x-ray source.

20. The method of claim 19 wherein the filter element comprises a solid filter foil contained within a linear bearing housing, with the magnet structure selectively positioning the solid filter foil in one of the non-filter position and the filter position.

21. The method of claim 19 wherein the filter element comprises a powderized filter material contained within an evacuated housing of the spectral filter, with the magnet structure selectively positioning the powderized filter material in one of the non-filter position and the filter position.

* * * * *